United States Patent
Schwint et al.

(10) Patent No.: US 10,081,581 B2
(45) Date of Patent: Sep. 25, 2018

(54) BUTADIENE EXTRACTION PRE-ABSORBER

(71) Applicant: Lummus Technology Inc., Bloomfield, NJ (US)

(72) Inventors: Kevin John Schwint, Long Valley, NJ (US); Robert John Brummer, Wharton, NJ (US)

(73) Assignee: Lummus Technology Inc., Bloomfield, NJ (US)

(*) Notice: Subject to any disclaimer, the term of this patent is extended or adjusted under 35 U.S.C. 154(b) by 39 days.

(21) Appl. No.: 15/204,167

(22) Filed: Jul. 7, 2016

(65) Prior Publication Data

US 2016/0311733 A1 Oct. 27, 2016

Related U.S. Application Data

(62) Division of application No. 14/030,186, filed on Sep. 18, 2013, now Pat. No. 9,403,739.

(Continued)

(51) Int. Cl.
| | |
|---|---|
| *C07C 7/10* | (2006.01) |
| *C07C 7/11* | (2006.01) |
| *B01D 3/14* | (2006.01) |
| *B01D 3/40* | (2006.01) |
| *C07C 4/02* | (2006.01) |

(Continued)

(52) U.S. Cl.
CPC ............. *C07C 7/10* (2013.01); *B01D 3/143* (2013.01); *B01D 3/40* (2013.01); *C07C 4/02* (2013.01); *C07C 5/327* (2013.01); *C07C 5/48* (2013.01); *C07C 7/11* (2013.01); *Y10T 29/49716* (2015.01)

(58) Field of Classification Search
None
See application file for complete search history.

(56) References Cited

U.S. PATENT DOCUMENTS

| 3,232,849 A | 2/1966 | Renberg et al. |
|---|---|---|
| 3,232,850 A | 2/1966 | Renberg et al. |
| | (Continued) | |

FOREIGN PATENT DOCUMENTS

| CN | 1298375 A | 6/2001 |
|---|---|---|
| JP | 2009-542886 A | 12/2009 |
| | (Continued) | |

OTHER PUBLICATIONS

Written Opinion issued in corresponding Chilean Application No. 716-2015 with English translation dated Sep. 14, 2016 (14 pages).

(Continued)

*Primary Examiner* — Tam M Nguyen
(74) *Attorney, Agent, or Firm* — Osha Liang LLP

(57) ABSTRACT

A process for recovering butadiene from a $C_4$ fraction is disclosed. The process may include: contacting a mixed $C_4$ stream comprising butane, butene, and butadiene, with a solvent comprising an organic solvent and water in a butadiene pre-absorber column to recover an overheads fraction comprising at least a portion of the butane, butene, and water, and a first bottoms fraction comprising the organic solvent, butadiene, and at least a portion of the butene; and feeding the first bottoms fraction to a butadiene extraction unit to recover a butene fraction, a crude butadiene fraction, and a solvent fraction.

13 Claims, 2 Drawing Sheets

Related U.S. Application Data

(60) Provisional application No. 61/703,409, filed on Sep. 20, 2012.

(51) Int. Cl.
    *C07C 5/327*     (2006.01)
    *C07C 5/48*     (2006.01)

(56) References Cited

U.S. PATENT DOCUMENTS

| | | | |
|---|---|---|---|
| 3,284,339 A | 11/1966 | Begley et al. | |
| 4,310,388 A | 1/1982 | Volkamer et al. | |
| 6,337,429 B1 | 1/2002 | Kindler et al. | |
| 7,132,038 B2 | 11/2006 | Bohner et al. | |
| 7,226,527 B2 | 6/2007 | Bohner et al. | |
| 7,393,992 B2 | 7/2008 | Hill et al. | |
| 7,482,500 B2 | 1/2009 | Johann et al. | |
| 7,495,138 B2 | 2/2009 | Crone et al. | |
| 2006/0235257 A1* | 10/2006 | Bridges | C07C 7/08 585/810 |
| 2008/0228019 A1* | 9/2008 | Heida | C07C 7/08 585/324 |
| 2009/0105514 A1* | 4/2009 | Lee | B01D 3/40 585/808 |
| 2010/0298621 A1 | 11/2010 | Bridges et al. | |
| 2012/0226087 A1* | 9/2012 | Kostova | C07C 7/04 585/810 |
| 2014/0081066 A1* | 3/2014 | Schwint | C07C 7/11 585/810 |
| 2014/0121437 A1* | 5/2014 | Schwint | C07C 7/08 585/810 |
| 2014/0200381 A1* | 7/2014 | Josch | C07C 7/05 585/621 |
| 2014/0296589 A1* | 10/2014 | Krupa | C07C 7/005 585/256 |
| 2015/0376091 A1* | 12/2015 | DiGiulio | C07C 5/48 585/621 |
| 2016/0152531 A1* | 6/2016 | Walsdorff | C07C 5/48 585/621 |
| 2016/0256815 A1* | 9/2016 | Kim | B01D 53/1418 |

FOREIGN PATENT DOCUMENTS

| | | |
|---|---|---|
| SU | 725552 A3 | 3/1980 |
| WO | 2011/110562 A1 | 9/2011 |

OTHER PUBLICATIONS

Written Opinion issued in Chilean Application No. 2015000716; dated Apr. 28, 2017 (7 pages).
Office Action issued in corresponding European Application No. 13839087.7 dated Aug. 28, 2017 (5 pages).
Decision of Grant issued in Russian Application No. 2015114484; dated Jun. 22, 2016 (16 pages).
International Search Report and Written Opinion dated Nov. 25, 2013 in corresponding International Application No. PCT/US2013/054909 (9 pages).
First Office Action dated Dec. 4, 15 issued by the State Intellectual Property Office in related Chinese Patent Application No. CN-201380051521.3 (6 pages).
Written Opinion dated Jan. 5, 2016 in corresponding Singapore application No. 11201502147S (7 pages).
Extended European Search Report dated Apr. 18, 2016 in corresponding European application No. 13839087.7 (6 pages).
Office Action dated Mar. 30, 2016 in corresponding Canadian application No. 2,885,707 (4 pages).
Notification of Reasons for Rejection dated Jun. 28, 2016 in corresponding Japanese application No. 2015-533067 (w/translation) (9 pages).
Notification of Reasons for Rejection dated Dec. 20, 2016 in corresponding Japanese application No. 2015-533067 (w/translation) (6 pages).

* cited by examiner

BUTADIENE EXTRACTION PRE-ABSORBER

CROSS-REFERENCE TO RELATED APPLICATION

This application, pursuant to 35 U.S.C. § 120, claims benefit to U.S. patent application Ser. No. 14/030,186 filed Sep. 18, 2013, now U.S. Pat. No. 9,403,739, which pursuant to 35 U.S.C. § 119(e), claims priority to U.S. Provisional Application Ser. No. 61/703,409, filed Sep. 20, 2012. Each of these applications is incorporated herein by reference in their entirety.

FIELD OF THE DISCLOSURE

Embodiments disclosed here relate to recovery of butadiene from a mixed hydrocarbon stream. More specifically, embodiments disclosed herein relate to recovery of a crude butadiene stream from a mixed C4 hydrocarbon stream using a butadiene pre-absorber column which may be integrated with an extractive distillation column for the efficient recovery of butadiene.

BACKGROUND

Butadiene is an important base chemical and is used, for example, to prepare synthetic rubbers (butadiene homopolymers, styrene-butadiene-rubber or nitrile rubber) or for preparing thermoplastic terpolymers (acrylonitrile-butadiene-styrene copolymers). Butadiene is also converted to sulfolane, chloroprene and 1,4-hexamethylenediamine (via 1,4-dichlorobutene and adiponitrile). Dimerization of butadiene also allows vinylcyclohexene to be generated, which can be dehydrogenated to form styrene.

Butadiene can be prepared from saturated hydrocarbons by refining process or by thermal cracking (steam cracking) processes, in which case naphtha is typically used as the raw material. In the course of refining or steam cracking of naphtha, a mixture of methane, ethane, ethene, acetylene, propane, propene, propyne, allene, butenes, butadiene, butynes, methylallene, $C_4$ and higher hydrocarbons are obtained.

Typical processes to recover butadiene from mixed $C_4$ streams include extractive distillation processes, which may incorporate use of selective solvents. Examples of extractive distillation processes are found, for example, in U.S. Pat. Nos. 7,393,992, 7,482,500, 7,226,527, 4,310,388, and 7,132,038, among others.

The butadiene recovery processes typically use 3- or 4-column extractive distillation systems to separate a mixed C4 stream into three product fractions, including a lights/butane/butenes stream (Raffinate-1 product), a crude butadiene product, which may be sent to a conventional distillation system for further purification, and a concentrated C4 acetylenes stream, which may be sent to a selective hydrogenation unit or recycled to a cracker. The columns used may include a main wash column, a rectifier column, which is typically physically built separately from the wash column due to height limitations, and an afterwash column, which may be combined with the rectifier column in a divided wall column design.

To increase butadiene recovery from such processes, a conventional stand-alone pre-fractionator may be used to increase the butadiene concentration of the dilute feed by conventional distillation. Disadvantages of using conventional distillation pre-fractionation include the technical difficulty and cost associated with separating the butanes/butenes and butadiene, which have relatively low volatility.

Another proposed method to increase butadiene recovery has been to incorporate a stand-alone scrubber/stripper system to process the feed gas, concentrating the butadiene in the feed gas by removing a portion of the butanes/butenes. Disadvantages of using a scrubber/stripper to process the feed stream include equipment costs.

In addition, butadiene extraction units may be partially debottlenecked or expanded by replacing the existing trays (valve or sieve) with random packing (for example, IMTP® High Performance Random Packing available from Koch-Glitsch LP, Wichita, Kans.), or replacing the existing packing with higher efficiency packing (for example, Raschig Super-Rings available from Raschig GmbH, Ludwigshafen) in all 3 (or 4) columns in the extractive distillation area. Disadvantages of high efficiency packing include its inability to increase capacity past a certain point. For example, replacing trays with IMTP packing generally will allow a 25 to 40% increase in capacity, and replacing IMTP packing with high-capacity packing will generally allow an additional 10 to 15% increase in capacity. Also, the conventional distillation area must also be further debottlenecked or expanded to a corresponding degree.

SUMMARY

Embodiments disclosed herein provide improved processes for preparing butadiene from dilute streams of mixed $C_4$ hydrocarbons. More specifically, embodiments disclosed herein provide for the recovery of a crude butadiene stream from a mixed C4 hydrocarbon stream using a butadiene pre-absorber column, which may be integrated with an extractive distillation column, allowing for the efficient recovery of butadiene.

In one aspect, embodiments disclosed herein relate to a process for recovering butadiene from a $C_4$ fraction. The process may include: contacting a mixed $C_4$ stream comprising butane, butene, and butadiene, with a solvent comprising an organic solvent and water in a butadiene pre-absorber column to recover an overheads fraction comprising at least a portion of the butane, butene, and water, and a first bottoms fraction comprising the organic solvent, butadiene, and at least a portion of the butene; and feeding the first bottoms fraction to a butadiene extraction unit to recover a butene fraction, a crude butadiene fraction, and a solvent fraction.

The butadiene extraction unit may comprise, for example, a main wash column and a rectifier/afterwash column. The pre-absorber bottoms fraction may then be contacted with additional solvent comprising the organic solvent and water in the main wash column to recover an overheads fraction comprising the butene and at least a portion of the water and a second bottoms fraction comprising the organic solvent and butadiene. The butadiene from the organic solvent may then be separated in the rectifier/afterwash column to recover the solvent fraction and the crude butadiene fraction. The solvent recovered, or a portion thereof, may then be recycled to the pre-absorber column and the main wash column as the organic solvent.

In other embodiments, the pre-absorber and the main wash column may share a common overhead system. For example, the overheads fraction comprising at least a portion of the butane, butene, and water and the overheads fraction comprising the butene and at least a portion of the water may be fed to a common overhead condensation system for condensing at least a portion of the combined overheads stream.

The mixed C4 hydrocarbon stream may be provided by at least one of cracking, oxidatively dehydrogenating, and non-oxidatively dehydrogenating a $C_4$ hydrocarbon stream comprising butane in one or more dehydrogenation reactors to produce a product gas stream comprising butane, butene, and butadiene. In such a case, a portion of one or both of the overheads fraction comprising at least a portion of the butane, butene, and water and the overheads fraction comprising the butene and at least a portion of the water may be recycled to the upstream butadiene production process, such as to the one or more dehydrogenation reactors.

In some embodiments, the butadiene pre-absorber column may be operated such that the concentration of butadiene relative to the total C4 hydrocarbons in the first bottoms fraction is at least 40 percent by weight. In various embodiments, the organic solvent comprises N-methyl pyrrolidone.

In another aspect, embodiments disclosed herein relate to a process for retrofitting a butadiene extraction system for recovering butadiene from a mixed C4 stream comprising butane, butene, and butadiene, the system comprising a main wash column for contacting a gaseous mixed C4 stream with a solvent or solvent mixture to recover an overheads fraction comprising butane and butene and a bottoms fraction comprising butadiene and the solvent or solvent mixture. The process for retrofitting may include: installing a butadiene pre-absorber column for contacting the gaseous mixed C4 stream with the solvent or solvent mixture to recover an overheads fraction comprising butane and butene and a bottoms fraction comprising butadiene, at least a portion of the butene, and the solvent or solvent mixture; fluidly connecting the butadiene pre-absorber column with the main wash column for contacting the bottoms fraction with additional solvent to recover an overheads fraction comprising the butene and a bottoms fraction comprising the butadiene, the solvent, and the additional solvent; and installing a liquid distributor in the main wash column to distribute the bottoms fraction fed to the main wash column. In some embodiments, the retrofitting process may also include fluidly connecting the butadiene pre-absorber to an existing overhead system of the main wash column.

In another aspect, embodiments disclosed herein relate to a system for recovering butadiene from a mixed $C_4$ hydrocarbon fraction. The system may include: a butadiene pre-absorber column for contacting a mixed $C_4$ stream comprising butane, butene, and butadiene, with a solvent comprising an organic solvent and water to recover an overheads fraction comprising at least a portion of the butane, butene, and water, and a first bottoms fraction comprising the organic solvent, butadiene, and at least a portion of the butene; and a butadiene extraction unit for separating the first bottoms fraction to recover a butene fraction, a crude butadiene fraction, and a solvent fraction.

The butadiene extraction unit may also include a main wash column for contacting the bottoms fraction with additional solvent comprising the organic solvent and water to recover an overheads fraction comprising the butane and at least a portion of the water and a second bottoms fraction comprising the organic solvent and butadiene; and a rectifier/afterwash column for separating the butadiene from the organic solvent to recover the solvent fraction and the crude butadiene fraction. In various embodiments, the system may also include: one or more fluid conduits for recycling at least a portion of the solvent fraction to the pre-absorber column and the main wash column as the organic solvent; one or more overheads condensation systems for condensing at least a portion of i) the overheads fraction comprising at least a portion of the butane, butene, and water, ii) the overheads fraction comprising the butene and at least a portion of the water, or iii) a combined overheads stream comprising an admixture of i) and ii); one or more reactors for at least one of cracking, oxidatively dehydrogenating, and non-oxidatively dehydrogenating a $C_4$ hydrocarbon stream comprising butane in to produce a product gas stream comprising butane, butene, and butadiene, and a fluid conduit for feeding at least a portion of the product gas stream to the butadiene pre-absorber column; one or more fluid conduits for recycling at least a portion of one or both of the overheads fraction comprising at least a portion of the butane, butene, and water and the overheads fraction comprising the butane and at least a portion of the water to the one or more reactors; and/or a control system for operating the butadiene pre-absorber column such that the concentration of butadiene relative to the total C4 hydrocarbons in the first bottoms fraction is at least 40 percent by weight.

Other aspects and advantages will be apparent from the following description and the appended claims.

DETAILED DESCRIPTION

Embodiments disclosed here relate to recovery of butadiene from a mixed hydrocarbon stream. More specifically, embodiments disclosed herein relate to recovery of a crude butadiene stream from a mixed C4 hydrocarbon stream using a butadiene pre-absorber column that may be integrated with an extractive distillation column for the efficient recovery of butadiene. It has been found that the extractive distillation process for the recovery of butadiene may be greatly improved by the integration of a pre-absorber column and wash column, and may result in energy and/or separation efficiency allowing for high processing rates and expansion of existing butadiene recovery processes.

Figure 1:
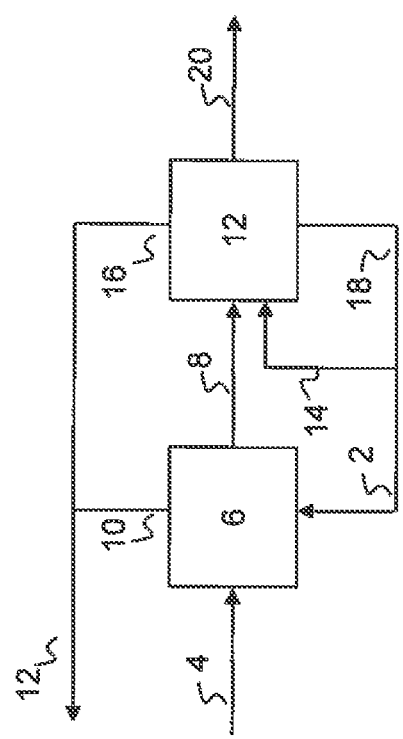
FIG. 1 is a simplified flow diagram of a process for butadiene recovery according to embodiments herein.

Referring now to FIG. 1, a simplified process flow diagram for recovering butadiene from a C4 fraction according to embodiments disclosed herein is illustrated. A selective solvent and a mixed C4 stream including butanes (n-butane and/or isobutane), butenes (1-butene, 2-butene, and/or isobutene), and butadienes (1,2-butadiene and/or 1,3-butadiene) may be fed via flow lines 2 and 4, respectively, to a butadiene pre-absorber column 6. Pre-absorber column 6, in some embodiments, may be a single-column absorber, reboiled and refluxed (not illustrated). In the pre-absorber column 6, the mixed C4 stream is contacted over appropriate internals with the selective solvent, resulting in at least a portion of the butadiene being absorbed in the selective solvent. A portion of the butenes and/or butanes may also be absorbed by the selective solvent. In some embodiments, the extractive distillation in the pre-absorber column 6 may partially or fully saturate the selective solvent with butadiene.

The extractive distillation of the mixed $C_4$ stream in the pre-absorber column 6 may be operated in such a way that the components of the mixed $C_4$ stream for which the selective solvent has a lower affinity than for butadiene, in particular the butanes and the butenes, remain essentially in the gas phase, while butadiene and further hydrocarbons for which the selective solvent has a higher affinity than for butadiene are virtually completely absorbed by the selective solvent. An overhead fraction including the non-absorbed portion of the butanes and butenes may be recovered from pre-absorber column 6 via flow line 10 (Raffinate-1A).

The selective solvent and extracted butadiene may be recovered as a bottoms fraction from the pre-absorber column 6 via flow line 8. The bottoms fraction, including the absorbed butadiene, may then be fed via flow line 8 to a butadiene extraction unit 12 for contact with additional selective solvent fed via flow line 14 over appropriate internals to further separate the butadiene from the butane and butenes and for separation of the butadiene from the selective solvent. For example, butadiene extraction unit 12 may include a main wash column, a rectifier, and an afterwash column (not illustrated). Other configurations for butadiene extraction units may also be used. Three product fractions may be recovered from the butadiene extraction unit 12, including a butane/butene fraction 16 (Raffinate-1B), a selective solvent fraction 18, and a crude butadiene fraction 20. At least a portion of the selective solvent fraction 18 may be recycled to the wash column in butadiene extraction unit 12 and/or the pre-absorber column 6.

In some embodiments, the Raffinate-1A and 1B fractions (butane/butene fraction 16 and overhead fraction 10) may be combined and recycled to a cracking process or dehydration process for production of additional butadiene. The combined Raffinate-1 fractions may be a gaseous stream including an enhanced amount of n-butane and 2-butene relative to the C4 feed. For example, the combined Raffinate-1 stream including butane and butene may contain from 50 to 100 volume % n-butane, from 0 to 50 volume % 1-butene and 2-butene, and from 0 to 3 volume % other constituents such as isobutane, isobutene, propane, propylene and $C_{5+}$ hydrocarbons.

In some embodiments, the crude butadiene fraction 20, which may contain greater than 80%, greater than 90%, or greater than 95% by weight butadiene, with the balance being impurities, may be fractionated to result in a "pure" butadiene stream, which may contain greater than 99%, greater than 99.5%, or greater than 99.7% butadiene, with the balance being impurities.

In the process as illustrated in FIG. 1, the absorbed 1,3-butadiene is concentrated relative to the absorbed butanes and butenes in the bottoms fraction 8. The absorbed C4s are then fed to a main wash column pre-absorbed in the selective solvent, thus making the required separations in the main wash column and rectifier less difficult, due to the higher 1,3-butadiene concentration, and more efficient, as the feed is already saturated. The balance of the butanes and butenes are then removed in the main wash column as a distillate product. The integration of a pre-absorber with the main wash column reduces separation difficulties, providing for energy efficiency, solvent usage efficiencies, and improved separation efficiency, allowing for increased overall throughput for a given main wash column design (with vs. without a pre-absorber).

The C4 fraction to be used as starting mixture in the present processes is a mixture of hydrocarbons having predominantly four carbon atoms per molecule. C4 fractions are obtained, for example, in the preparation of ethylene and/or propylene by thermal or catalytic cracking of a petroleum fraction, such as liquefied petroleum gas, light naphtha or gas oil. C4 fractions may also be obtained by the catalytic dehydrogenation (oxidative and/or non-oxidative dehydrogenation) of n-butane and/or n-butene. The resulting C4 fractions generally include butanes, n-butene, isobutene, 1,3-butadiene and small amounts of C3 and C5 hydrocarbons, as well as butynes, in particular 1-butene (ethylacetylene) and butenyne (vinylacetylene). The 1,3-butadiene content is generally from 5 to 80% by weight. For example, a cracker or a CATADIENE unit may contain 15 to 17% butadiene, by weight. Other mixed C4 feed streams may contain greater or lesser amounts of butadiene. When present in the mixed feed stream, vinylacetylene may be selectively hydrogenated to the desired 1,3-butadiene product prior to feed of the mixed C4 stream to the pre-absorber.

Selective solvents may include butyrolactone, nitriles such as acetonitrile, propionitrile, methoxypropionitrile, ketones such as acetone, furfural, N-alkyl-substituted lower aliphatic amides such as dimethylformamide, diethylformamide, dimethylacetamide, diethylacetamide, N-formylmorpholine, N-alkyl-substituted cyclic amides (lactams) such as N-alkylpyrrolidones, especially N-methylpyrrolidone (NMP). In some embodiments, alkyl-substituted lower aliphatic amides or N-alkyl-substituted cyclic amides, dimethylformamide, acetonitrile, furfural or NMP are used.

In some embodiments, it is also possible to use mixtures of these extractants with one another, for example of NMP and acetonitrile, mixtures of these extractants with cosolvents and/or tert-butyl ethers, e.g. methyl tert-butyl ether, ethyl tert-butyl ether, propyl tert-butyl ether, n- or isobutyl tert-butyl ether. In other embodiments, NMP may be in aqueous solution, with from 0 to about 20 weight % water, or with from 7 to 10 weight % water, or with 8 to 8.5 weight % water in other embodiments.

Figure 2:
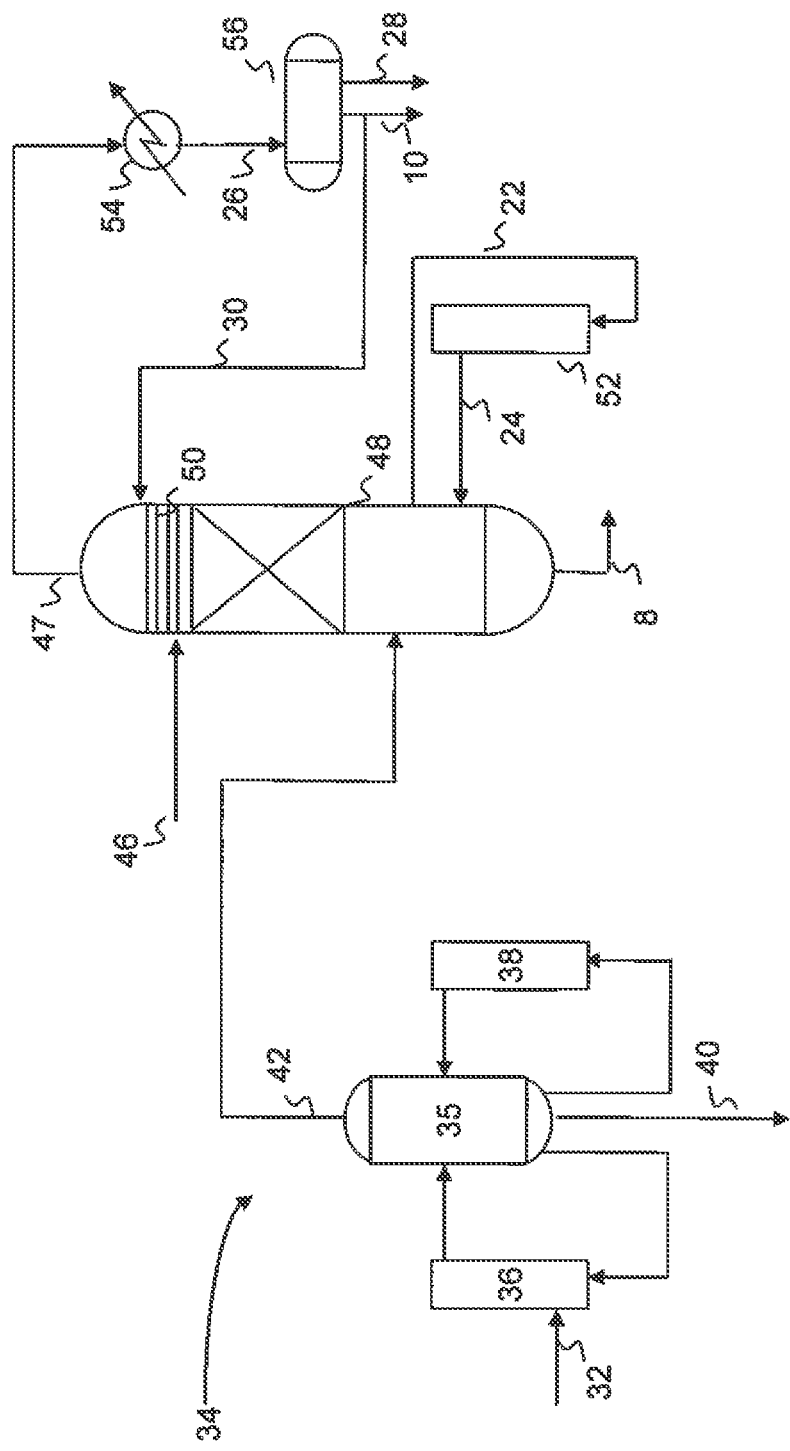
FIG. 2 is a simplified flow diagram of a process for butadiene recovery according to embodiments herein.

Referring now to FIG. 2, a simplified process flow diagram of a butadiene pre-absorber according to embodiments disclosed herein is illustrated. A mixed $C_4$ stream 32 may be fed to a vaporization system 34, which may include a vaporization drum 35 and one or more heat exchangers (feed vaporizers) 36, 38 to vaporize the mixed C4 feed. An intermittent blow down may be taken from vaporization drum 35 to remove heavies that would otherwise build up in the drum. The vaporized $C_4$s are recovered via flow line 42 and fed to the bottom of the butadiene pre-absorber 48, where they are contacted with a portion of the cold, lean solvent fed via flow line 46. Several wash trays 50 are provided at the top of butadiene pre-absorber 48 to ensure that solvent does not contaminate raffinate 10, as well as to minimize solvent losses.

The pre-absorber overheads 47 has an enhanced concentration of butanes and butanes, along with some water; trace concentrations of 1,3-butadiene may also be present. The pre-absorber overheads 47 is condensed in condenser 54, which may be a total or partial condenser, and drains into the accumulator 56. Water 28 is decanted and removed in the boot of accumulator 56.

A portion of mixed $C_4$s and solvent is removed from the column by way of stream 22 and fed to a reboiler 52. Reboiler 52 provides additional vapor traffic in butadiene pre-absorber 48, which enhances hydrocarbon separation (i.e., extractive distillation). In some embodiments, reboiler 52 may be used to control the concentration of 1,3-butadiene relative to $C_4$s at about 40 weight % (for example, in the case of dilute feed), or higher (for example, in the case of debottleneck/expansions), where the control may be provided via a DCS control system, for example. Reboiler 52, for example, may be a total, once-through reboiler that has a small percent vaporization and small temperature rise in the case of dilute feed. In the case of debottleneck/expansions, where high 1,3-butadiene concentrations are achieved, a suppressed vaporization reboiler design option, similar to a rectifier reboiler design, is available.

A portion of the condensed overheads, the hydrocarbons recovered in drum 56, are refluxed via stream 30 to the wash trays of butadiene pre-absorber 48. The reflux of hydrocarbons provided via stream 30 washes the butadiene pre-absorber 48 overheads, limiting uptake of solvent, and also provides a measure of control for the hydrocarbon composition profile in butadiene pre-absorber 48. The remaining portion of the condensed overheads, primarily butanes and butenes, being less soluble in the solvent than 1,3-butadiene, are removed from drum 56 as raffinate 10.

The absorbed 1,3-butadiene is thus concentrated in the pre-absorber bottoms 8 relative to the feed concentration. The $C_4$s may then be fed to a butadiene extraction system (not illustrated), which may include a main wash column, a rectifier, and an afterwash column, as they are already optimally "preabsorbed" in liquid solvent. The extractive distillation that may occur in the main wash column of the butadiene extraction unit is now more efficient and less costly due to a higher 1,3-butadiene concentration, and because the pre-absorber bottoms 8 is already saturated. In a wash column, the balance of the butanes and butenes may be removed as a distillate product.

The main wash column may have, for example, from 5 to 15, or from 8 to 10, theoretical plates, and a backwash zone having, for example, 4 theoretical plates. The backwash zone serves to recover the butadiene present in the gas phase by means of liquid hydrocarbon reflux, for which the top fraction is condensed beforehand. The internals provided are structured packing, trays, or random packing. The pressure at the top of the column may be, for example, 1 to 2 bara. The temperature in the bottom of the column may be, for example, from 130 to 150° C.

The extraction solution (selective solvent+absorbed butadiene and other hydrocarbons) from the main wash column may be transferred to a desorption zone, where the butadiene may be desorbed from the selective solvent. The desorption zone may have a reduced pressure and/or elevated temperature compared to the pre-absorber and/or main wash column, for example. The work-up of the selective solvent laden with butadiene (and further hydrocarbons for which the selective solvent has a higher affinity than for butadiene) recovered from the main wash column may be carried out by fractional desorption, with the hydrocarbons absorbed in the selective solvent being desorbed in the reverse order of their affinity for the selective solvent. In some embodiments, the pre-absorber rosy be integrated with an existing butadiene extraction unit, such as described in U.S. Pat. No. 7,482,500, for example.

As noted above, existing butadiene extraction systems may be retrofitted to include a pre-absorber, such as that illustrated in FIG. 2. In some embodiments, the butadiene pre-absorber shown in FIG. 2 may be integrated with a pre-existing butadiene extraction unit. In some embodiments, the wash column, rectifier and degasser in a pre-existing butadiene extraction unit obtaining feed from butadiene pre-absorber 48 may require a liquid feed distributor and adjustments to the locations of their feed due to the $C_4$s in the pre-absorber bottoms 20 being pre-absorbed in the liquid solvent. For example, a process for retrofitting a butadiene extraction system for recovering butadiene from a mixed C4 stream may include installing a butadiene pre-absorber column for contacting the gaseous mixed C4 stream with the solvent or solvent mixture to recover an overheads fraction comprising butane and butene and a bottoms fraction comprising butadiene, at least a portion of the butene, and the solvent or solvent mixture; fluidly connecting the butadiene pre-absorber column with the main wash column for contacting the bottoms fraction with additional solvent to recover an overheads fraction comprising the butene and a bottoms fraction comprising the butadiene, the solvent, and the additional solvent; and installing a liquid distributor in the main wash column to distribute the bottoms fraction fed to the main wash column. In other embodiments, retrofitting an existing unit may also include fluidly connecting the butadiene pre-absorber to an existing overhead system of the main wash column of the existing butadiene extraction system.

Retrofitting an existing process as described above, to include a pre-absorber according to embodiments disclosed herein, may allow for a greater than 40% expansion of capacity, such as up to 50%, 60%, 75%, 90%, 100% or even a greater than 100% increase in capacity over existing plant capacity. Without the butadiene pre-absorber process, plant debottlenecks or expansions (without additional trains) of pre-existing butadiene extraction processes, such as those incorporating a conventional pre-fractionator or a scrubber/stripper system could typically achieve only a 40% expansion at most.

Further with regard to retrofitting an existing butadiene extraction process, in some embodiments, the existing main washer may be used as the pre-absorber together with a new larger main washer, to achieve an even greater increase in capacity.

EXAMPLE

In Table 1, a process using a conventional butadiene extraction unit is compared to the same butadiene extraction unit having a butadiene pre-absorber similar to that shown in FIG. 2. In this Example, the overhead system of the butadiene pre-absorber is integrated with the overhead system of the wash column.

TABLE 1

| Variable\Case | Conventional Butadiene Extraction Unit | With Pre-Absorber |
|---|---|---|
| Solvent to Pre-Absorber | N/A | 67,835 kg/h |
| Solvent to Main Wash | 170,150 kg/h | 66,700 kg/h |
| Solvent to Aftenvasher | 43,350 kg/h | 43,035 kg/h |
| Total Solvent Flow | 213,500 kg/h | 177,570 kg/h |
| Pre-Absorber Reboiler Duty | N/A | 0.53 mm kcal/h |
| Rectifier Reboiler Duty | 6.4 mm kcal/h | 5.50 mm kcal/h |
| Degasser Reboiler Duty | 6.2 mm kcal/h | 5.25 mm kcal/h |
| Total Stripping Duty | 12.7 mm kcal/h | 11.28 mm kcal/h |

As shown in Table 1, it is anticipated that the energy efficiency with a pre-absorber according to embodiments disclosed herein may be much greater than any previous design, such as a conventional pre-fractionator or a scrubber/stripper system, due in part to the vaporizers and reboilers incorporated in the butadiene pre-absorber process. Solvent usage is also significantly decreased for an equivalent 1,3-butadiene production rate.

The pre-absorbers according to embodiments disclosed herein may be controlled using only one hard specification, 1,3-butadiene content in the distillate, with no hard spec for the butadiene pre-absorber bottoms. This allows for an easier separation control scheme than when hard specifications are used for both the overheads and bottoms.

Advantageously, the use of pre-absorbers according to embodiments disclosed herein may provide for the processing of dilute mixed $C_4$ streams with high efficiency. For example, at equivalent butadiene rates, use of a pre-absorber according to embodiments disclosed herein may provide for 16.8% lower overall solvent rates and 11% less utilities, such as shown in Table 1 above, over conventional butadiene extraction systems. Greater efficiencies may also be realized, depending upon plant capacity and design. Such benefits may be realized using minimal plot area.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed:

1. A process for retrofitting a butadiene extraction system for recovering butadiene from a mixed C4 stream comprising butane, butene, and butadiene, the system comprising a main wash column for contacting a gaseous mixed C4 stream with a solvent or solvent mixture to recover an overheads fraction comprising butane and butene and a bottoms fraction comprising butadiene and the solvent or solvent mixture, the process for retrofitting comprising:

installing a butadiene pre-absorber column and an associated fluid conduit for receiving and contacting the gaseous mixed C4 stream with the solvent or solvent mixture to recover a first overheads fraction comprising butane and butene and a first, liquid, bottoms fraction comprising butadiene, at least a portion of the butene, and the solvent or solvent mixture; and fluidly connecting the butadiene pre-absorber column with the existing main wash column for contacting the first bottoms fraction with additional solvent to recover a second overheads fraction comprising the butene and a second bottoms fraction comprising the butadiene, the solvent, and the additional solvent.

2. The process of claim 1, further comprising fluidly connecting the butadiene pre-absorber to an existing overhead system of the main wash column.

3. The process of claim 1, further comprising installing a liquid distributor in the main wash column to distribute the bottoms fraction fed to the main wash column.

4. The process of claim 1, further comprising adjusting a feed location of one or more streams being fed to the main wash column.

5. The process of claim 1, further comprising installing one or both of a butadiene pre-absorber column overhead system and a pre-absorber column reboiler.

6. The process of claim 5, wherein the pre-absorber column reboiler comprises a once-through reboiler.

7. The process of claim 5, wherein the pre-absorber column reboiler comprises a suppressed vaporization reboiler.

8. The process of claim 5, wherein the pre-absorber column overhead system comprises a condenser, an accumulator, and a feed line to provide reflux to the pre-absorber column.

9. The process of claim 1, further comprising providing a control system for operating the butadiene pre-absorber column such that the concentration of butadiene relative to the total C4 hydrocarbons in the first bottoms fraction is at least 40 percent by weight.

10. A process for retrofitting a butadiene extraction system for recovering butadiene from a mixed C4 stream comprising butane, butene, and butadiene, the system comprising a main wash column for contacting a gaseous mixed C4 stream with a solvent or solvent mixture to recover an overheads fraction comprising butane and butene and a bottoms fraction comprising butadiene and the solvent or solvent mixture, the process for retrofitting comprising:

converting the main wash column to a butadiene pre-absorber column for contacting the gaseous mixed C4 stream with the solvent or solvent mixture to recover a first overheads fraction comprising butane and butene and a first bottoms fraction comprising butadiene, at least a portion of the butene, and the solvent or solvent mixture;

installing a new main wash column;

fluidly connecting the butadiene pre-absorber column with the new main wash column for contacting the first bottoms fraction with additional solvent to recover a second overheads fraction comprising the butene and a second bottoms fraction comprising the butadiene, the solvent, and the additional solvent.

11. The process of claim 10, further comprising fluidly connecting the new main wash column to a rectifier/afterwash column for separating the butadiene from the organic solvent to recover the solvent fraction and the crude butadiene fraction.

12. The process of claim 10, wherein the overhead system of the butadiene pre-absorber column is integrated with the overhead system of the new main wash column.

13. The process of claim 10, further comprising providing a control system for operating the butadiene pre-absorber column such that the concentration of butadiene relative to the total C4 hydrocarbons in the first bottoms fraction is at least 40 percent by weight.

* * * * *